United States Patent [19]

Kruse et al.

[11] Patent Number: 5,743,259

[45] Date of Patent: Apr. 28, 1998

[54] APPARATUS AND METHOD FOR CONTINUOUS MONITORING OF TISSUE CARBON DIOXIDE AND PH USING CAPNOMETRIC RECIRCULATING GAS TONOMETRY

[75] Inventors: James Alexander Kruse, Bloomfield Hills; Jorge Alberto Guzman, Southfield, both of Mich.

[73] Assignee: Wayne State University, Detroit, Mich.

[21] Appl. No.: 390,406

[22] Filed: Feb. 16, 1995

[51] Int. Cl.$^6$ ............................................. A61B 5/00
[52] U.S. Cl. ............................................. 128/632; 128/637
[58] Field of Search ............................ 128/632–635, 128/637, 664–665

[56] References Cited

U.S. PATENT DOCUMENTS

| | | |
|---|---|---|
| 4,643,192 | 2/1987 | Fiddian-Green . |
| 4,928,694 | 5/1990 | Maxwell . |
| 5,058,416 | 10/1991 | Engelhardt et al. . |
| 5,423,320 | 6/1995 | Salzman et al. . |
| 5,479,923 | 1/1996 | Rantala . |

OTHER PUBLICATIONS

Copy of Int'l Search Report from corresponding PCT case.
A461, vol. 83, Anesthesiology No. 3A 09/195, "A New Method for Continuous Intramucosal PCO$_2$-Measurement in the Gastrointestinal Tract".
A.M. Dawson, et al., "Small Bowel Tonometry: Assessment of Small Gut Mucosal Oxygen Tension in Dog and Man", 206 Nature 943–44 (1965).
A.B. Johan Groeneveld and Jeroen J. Kolkman, "Splanchnic Tonometry: A Reveiw of Physiology, Methodology, and Clinical Applications", Journal of Critical Care, vol. 9.
Cinda H. Clark and Guillermo Gutierrez, "Gastric Intramucosla pH: A Noninvasive Method for the Indirect Measurement of Tissue Oxygenation", Amer. Jrnl. of Crit. Care, vol. 1.

David R. Dantzker, "The Gastrointestinal Tract the Canary of the Body?", JAMA, Sep. 8, 1993—vol. 270, 1247–1248.
Michael C. Chang, et al., "Gastric Tonometry Supplements Information Provided by Systemic Indicators of Oxygen Transport", The Journal of Trauma, 488–494, 1994.
Paul E. Marik, "Gastric Intramucosal pH* A Better Predictor of Multioy0gan Dysfunction Syn. and Death than Oxygen–Derived Vari. in Pat. with Sepsis", Univ. of W. Ont., Oct. 27, 1992.
Nicholas Maynard, et al., "Assessment of Splanchnic Oxygenation by Gastric Tonometry in Patients with Acute Circulatory Failure", JAMA, vol. 270, No. 10, Sep. 8, 1993.
Guillermo R. Doglio, et al., "Gastric Mucosal pH as a Prognostic Index of Mortality in Critically Ill Patients", Critical Care Medicine, vol. 19, No. 8 1037–1040 (1991).
Comprehensive Instructions for Use, Trip NGS Catheter, Catalog No. 2002–48–16, Tonometrics, Inc.
James A. Kruse, et al., "Relationship between the Apparent Dissociation Constant of Blood Carbonic Acid and Severity of Illness", The Jrnl. of Lab. & Clin. Med., (1989).

*Primary Examiner*—John P. Lacyk
*Attorney, Agent, or Firm*—Brooks & Kushman P.C.

[57] ABSTRACT

A tonometry catheter apparatus comprising an elongate flexible tube having a proximal extracorporeal end and a distal interacorporeal end. The distal end of the tube has a distensible, gas-permeable tonometry vessel, the vessel and the distal end defining therebetween a space which may be filled with a gas. An in-flow orifice lies in communication with the space, through which gas may enter the vessel. An in-flow lumen with a distal end and a proximal end is also provided, the distal end being in communication with the in-flow orifice. An out-flow orifice lies in communication with the space, through which the gas may exit the vessel. An out-flow lumen is disposed with a distal end and a proximal end, the distal end being in communication with the out-flow orifice. The proximal end of the tube has a pump for propelling gas into the vessel. A capnometer and a sensor quantify the level of carbon dioxide ($CO_2$) gas exiting the vessel. A hollow connecting member defines with the vessel, the in-flow lumen and the out-flow lumen a closed path through which the gas may continuously recirculate.

20 Claims, 1 Drawing Sheet

APPARATUS AND METHOD FOR CONTINUOUS MONITORING OF TISSUE CARBON DIOXIDE AND PH USING CAPNOMETRIC RECIRCULATING GAS TONOMETRY

BACKGROUND OF THE INVENTION

1. Technical Field

This invention relates to a method and apparatus for continuous monitoring of tissue $pCO_2$ and tissue pH using capnometric recirculating gas tonometry.

2. Related Art

Most cells, tissues, and organs of the human body require oxygen to carry out their normal physiologic functions and to maintain viability. This oxygen is obtained from the atmosphere by the lungs, carried predominantly by hemoglobin molecules in the blood, and delivered to the cells, tissues, and organs of the body by the circulatory system. If the lungs can not provide sufficient oxygen to the blood, or if there is insufficient hemoglobin in the blood (i.e., anemia) to carry sufficient oxygen, or if the heart can not pump an adequate volume of blood over time to the various organs of the body, or if there is blockage of blood flow to one or more regions of the circulation, the affected cells will suffer from lack of adequate oxygen, a condition known as tissue hypoxia.

An important goal in the clinical management of critically ill patients is ensuring the adequacy of tissue oxygenation. A variety of means are in use to help achieve this goal. Among these, pulmonary artery catheterization is commonly used to allow determination of cardiac output, mixed venous oxygen saturation and partial pressure, and derivation of oxygenation transport variables such as systemic oxygen delivery, systemic oxygen consumption, and systemic oxygen extraction. However, these conventional hemodynamic and oxygen-derived parameters can be insensitive to mild, moderate, early, or compensated stages of perfusion failure and to regional tissue hypoperfusion, including ischemia, or hypoxia involving the gastrointestinal tract.

If tissue hypoxia is sufficiently severe, the hypoxic cells produce lactic acid. This allows the cells to produce needed energy in the absence of oxygen, and provides a temporary means of maintaining cellular function and viability. It is temporary because this excessive acid production results in a decrease of the pH within and around the cells, and this decrease in pH will itself eventually threaten the functional capacity and viability of the affected cells. Thus, detecting a decrease in the pH inside cells comprising a tissue or organ can serve as an indicator of tissue hypoxia.

Measurement of the pH of the cells lining the stomach (gastric intramucosal pH), intestines, or other organs or tissues of the body can be performed using a technique known as hollow viscus tonometry, in which a walled chamber is placed within a hollow organ such as the stomach. The walled chamber, which may be in the form of a balloon, is constructed of material that is permeable to carbon dioxide gas, but effectively impermeable to liquid. When filled with a liquid such as water or saline solution, and situated within the hollow viscus, such a balloon will allow the passage of carbon dioxide ($CO_2$) gas from the hollow viscus to pass through the membrane of the balloon and become dissolved in the liquid solution contained within the balloon. In time, the level of carbon dioxide in solution within the balloon will equal or be proportional to the level of carbon dioxide within the hollow viscus. Because biological membranes, including the membranes that compose the surface of the cells lining the stomach and other hollow organs, are also permeable to carbon dioxide, the level of carbon dioxide within the hollow viscus will, under certain undisturbed circumstances, be equal to or approximately equal to the level of carbon dioxide within the cells lining comprising the viscus.

Thus, if the liquid-filled balloon is allowed to sit within a hollow viscus such as the stomach or intestine for a sufficient period of time, and then the liquid is aspirated from the balloon by a catheter connected to the balloon, and then the liquid is analyzed in a laboratory to determine the level of carbon dioxide gas dissolved within the liquid, the level of carbon dioxide gas inside the cells lining the viscus (intramucosal $pCO_2$) can be ascertained. If intramucosal $pCO_2$ is known, then intramucosal pH can be determined using a mathematical formula that relates pH to $pCO_2$. This formula also requires that a third variable is known, namely the concentration of bicarbonate ions inside the cells comprising or lining the viscus. This intracellular bicarbonate concentration is equal to or approximately equal to the concentration of bicarbonate ions in arterial blood, serum, or plasma, and the latter can be readily determined by a blood test.

As is common clinical practice, this blood test is frequently performed in most hospitalized critically ill patients treated in the intensive care unit setting, often being performed daily or even several times each day. The bicarbonate concentration can be obtained by direct measurement, or calculated from the results of other blood tests using a mathematical equation (see Kruse J. A., Hukku P., Carlson R. W.: "Relationship Between The Apparent Dissociation Donstant Of Blood Carbonic Acid And Severity Of Illness," 114 Jnl of Laboratory & Clinical Medicine, 568–574 (1989).

According to information from scientific studies that have been reported in the published biomedical literature, tonometry is a useful means of evaluating splanchnic intramucosal $pCO_2$ and splanchnic intramucosal pH (pH within the cells lining or comprising certain portions of the gastrointestinal tract and certain adjacent organs or tissues; also known as pHi), thereby indirectly evaluating the adequacy of splanchnic blood flow and oxygenation. This technique has been shown to provide a sensitive and early indication of splanchnic ischemia, hypoperfusion, and hypoxia. The available information indicates that determination of tissue pH is a valuable prognostic indicator of survival among critically ill patients hospitalized in the intensive care unit setting, and that it is a better prognostic indicator than any of the conventional hemodynamic and oxygen-derived physiological variables.

U.S. Pat. No. 4,643,192 is illustrative of tonometric methods, and is incorporated herein by reference. An illustrative device is described in Catalog No. 2002-48-16, TRIP® NGS CATHETER, Tonometrics, Inc., Hopkinton, Mass., which is also incorporated herein by reference.

A major drawback of the previously described method of performing hollow viscus tonometry (using the device and technique briefly described above) is that it requires a specified period of time to arrive at the measurement result. Under ideal circumstances this time period is typically about one hour, but can be substantially longer in other circumstances. This obligatory time period is necessary because the events listed below must take place after the catheter has been placed within the body. All are required in order to arrive at a single value of tissue pH and/or tissue $pCO_2$. In the following, it is assumed that the organ in which the tonometry catheter has been placed is the stomach, although the same requirements are expected for placement in other parts of the body:

1. A measured volume of liquid must be carefully introduced through the tonometry catheter and into the balloon.

2. Carbon dioxide gas dissolved in the liquid residing within the tonometry balloon must reach or approach equilibrium with the carbon dioxide gas within the hollow of the stomach.

3. Liquid must be carefully aspirated from the tonometry balloon by the tonometry catheter. For accurate measurements, it may be necessary to ensure that the liquid within the dead space volume of the catheter tube is aspirated and discarded, prior to aspirating and collecting liquid that had resided within the balloon.

4. The aspirated liquid must be sealed within a gas-tight container. Prior to sealing, any air bubbles must be expelled from the container lest they alter the level of carbon dioxide dissolved in the liquid.

5. The liquid specimen must be transported to a laboratory or location where assay instruments are available to measure the level or partial pressure of carbon dioxide gas within the liquid specimen.

6. The aspirated liquid must be assayed for the level or partial pressure of carbon dioxide gas within the liquid specimen. A skilled laboratory technician is required to perform the laboratory analysis that measures the level of carbon dioxide dissolved in the liquid specimen.

7. If insufficient time was allowed for complete equilibration while the liquid was within the balloon (typically less than about 90 minutes), the result of the carbon dioxide assay must be mathematically adjusted to obtain an estimate of the steady-state (i.e., equilibrium) value. Even if the elapsed time was sufficient for complete equilibration, a mathematical adjustment is still required to account for the expected gradient between the level or partial pressure of carbon dioxide external to the balloon and the level or partial pressure of carbon dioxide dissolved in the liquid within the balloon.

8. Tissue pH must be mathematically derived from the adjusted value of the level or partial pressure of carbon dioxide dissolved in the liquid using the Henderson-Hasselbalch equation or a modification thereof.

The obligatory time for completing the above steps limits the frequency of the measurements and in some cases makes repeated measurements within a certain time frame impossible or impractical. In addition, each of the steps involved in the above techniques must be carried out by personnel specifically trained and skilled in the techniques. In addition, the techniques are cumbersome to perform. In addition, the elapsed time between filling the tonometry balloon with liquid and aspirating the liquid must be accurately determined so that the steady-state value of carbon dioxide within the balloon liquid can be accurately estimated from the measured value of carbon dioxide within the balloon liquid. In addition, the mathematics involved entail another level of understanding and training necessary to correctly obtain the final measurement value of tissue pH. This calculation generally requires the use of a calculating aid such as an electronic calculator or computer.

Besides the cumbersome sequence of techniques and the obligatory time needed to arrive at measurements of tissue pH, determination of tissue pH by this means at best provides only intermittent measurements, each isolated to a single point in time usually separated by a matter of hours. The existing art does not allow for a means of providing continuous or near-continuous measurements of tissue $pCO_2$ or tissue pH.

Other objects and advantages of the invention will become apparent upon reading the following detailed description and upon reference to the following drawings.

SUMMARY OF INVENTION

These drawbacks of conventional tonometry led us to develop and test an apparatus and method to allow continuous measurement of tissue pH and $pCO_2$ using capnometric recirculating gas tonometry (CRGT).

A continuous CRGT monitoring system has been devised using an improved vessel or balloon-tipped tube and an extracorporeal, gas-tight circuit containing a pump and $CO_2$ analyzer configured as a closed recirculation system.

The tonometry catheter of the present invention comprises an elongate flexible tube having a proximal extracorporeal end and a distal intracorporeal end. The catheter's distal end has a distensible, gas-permeable tonometry vessel situated adjacent thereto. The vessel defines a confined space at, near, or surrounding the distal end, which may be filled with a gas.

A vessel in-flow orifice lies in communication with the space, through which gas may enter the vessel space. An in-flow lumen is provided in the tube with a distal end and a proximal end. The distal end is in communication with the in-flow orifice.

A vessel out-flow orifice lies in communication with the space, through which the gas may leave the vessel. An out-flow lumen is provided in the tube with a distal end and a proximal end. The distal end is in communication with the out-flow orifice.

The catheter's proximal end is in communication with means for propelling gas into the vessel. In series with the propelling means is a capnometric device. The capnometric device is used to measure and display the level of carbon dioxide in the vessel and lumens of the circuit. A hollow connecting member links the propelling means, the capnometric device, and the lumens to define a closed path through which the gas may continuously recirculate.

BEST MODE(S) FOR CARRYING OUT THE INVENTION

Figure 1:
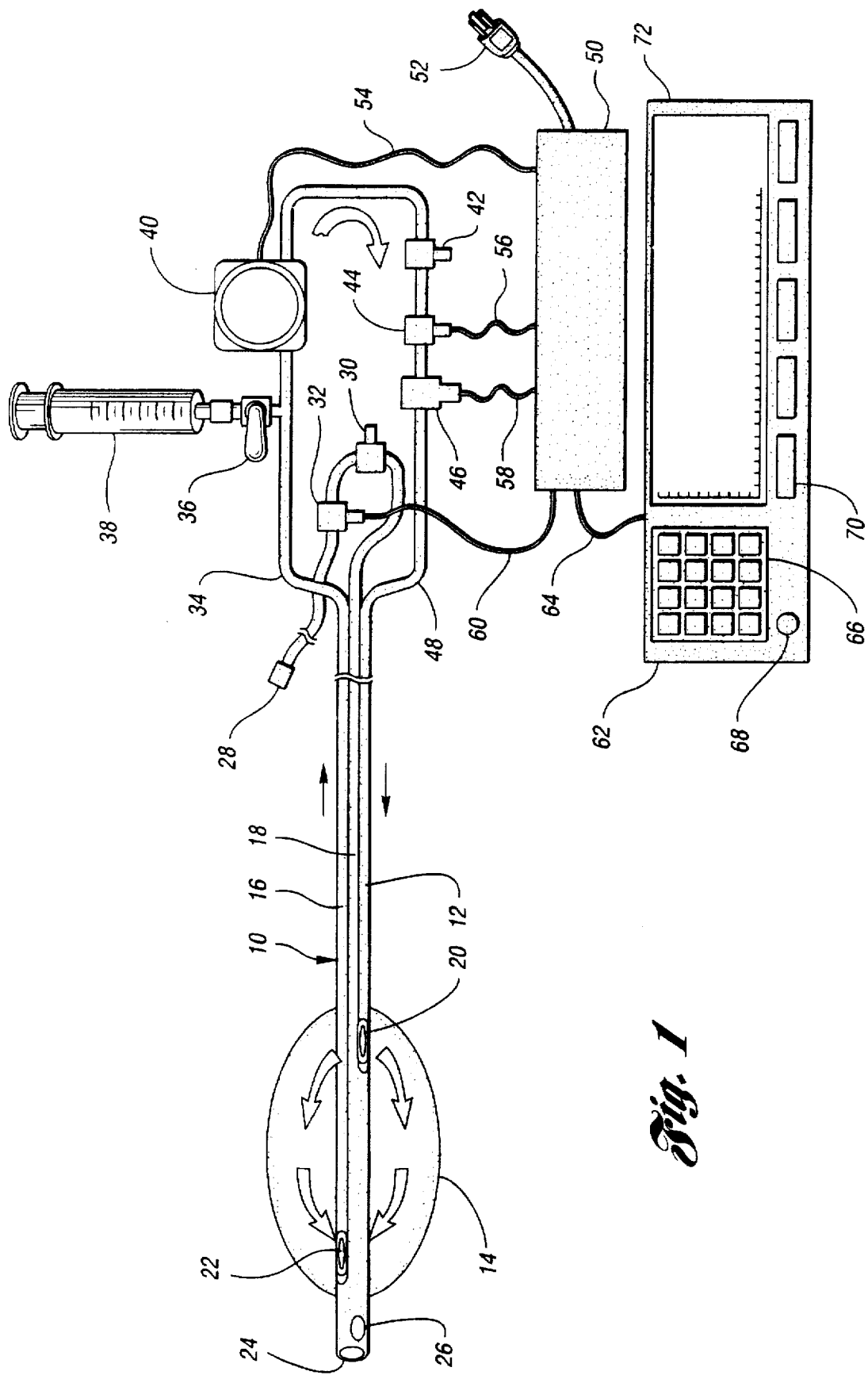
FIG. 1 is a schematic diagram of an improved tonometry catheter and closed circuit monitoring system.

We have developed and tested an apparatus and method to allow continuous measurement of tissue pH and/or $pCO_2$ using capnometric recirculating gas tonometry (CRGT). A continuous CRGT monitoring system has been devised using an improved vessel or balloon-tipped tube and an extracorporeal, gas-tight circuit containing a pump and $CO_2$ analyzer configured as a closed recirculation system.

The tonometry catheter of the present invention comprises an elongate flexible tube having a proximal extracorporeal end and a distal intracorporeal end. The catheter's distal end has a distensible or nondistensible, gas-permeable tonometry vessel situated adjacent thereto. The vessel defines a confined space surrounding the distal end, which may be filled with a gas.

A vessel in-flow orifice lies in communication with the space, through which gas may enter the vessel space. An in-flow lumen is provided in the tube with a distal end and a proximal end. The distal end is disposed in communication with the in-flow orifice.

A vessel out-flow orifice lies in communication with the space, through which the gas may leave the vessel. An out-flow lumen is provided in the tube with a distal end and a proximal end. The distal end is in communication with the out-flow orifice.

The catheter's proximal end is in communication with means for propelling gas into the vessel. In series with the propelling means is a capnometric device, used to measure and display the level of carbon dioxide in the lumens of the circuit. A hollow connecting member links the propelling means, the capnometric device, and the lumens to define a closed path through which the gas may continuously recirculate.

This novel method, and the novel device based on this method, provide a means for continuously ascertaining and displaying tissue $pCO_2$ and/or tissue pH.

The advantages of this invention is that it:

1. obviates the necessity of having skilled personnel carry out a cumbersome sequence of techniques to determine tissue $pCO_2$ and/or tissue pH.

2. obviates the time involved in determining tissue $pCO_2$ and/or tissue pH.

3. provides a continuous or near-continuous measurement of tissue $pCO_2$ and/or tissue pH, and/or the directional trend and rate of change of tissue $pCO_2$ and/or tissue pH.

4. obviates the need for handling liquid specimens aspirated from a catheter located inside the body.

5. obviates the need for transporting liquid specimens to the location of laboratory instruments capable of assaying carbon dioxide.

6. obviates the need for performing carbon dioxide analysis as a separate assay using a separate instrument or analyzer that is not part of the tonometry device, that may be located physically distant from the tonometry device, and that requires specially trained personnel to operate.

In addition, certain carbon dioxide analyzers that are commonly used in clinical laboratories have been shown to yield erroneous carbon dioxide assay results when used to measure the partial pressure of carbon dioxide in aspirated liquid specimens obtained from standard tonometry catheters. (See, e.g., Riddington, et al., "Potential Hazards In Estimation Of Gastric Intramucosal pH," 340 LANCET 547 (1992); Takala, et al., "Saline $PCO_2$ Is An Important Source Of Error In The Assessment Of Gastric Ontramucosal pH," 22 CRITICAL CARE MEDICINE 1877–79 (1994).) The novel method of measurement and monitoring described herein obviates this potential source of error.

1. The CRGT system. A commercially available, nasogastric tonometry catheter (TRIP NGS; Tonometrics, Inc; Hopkinton, Mass.) was improved to allow continuous recirculation of gas through the vessel. The improvement includes the incorporation of a second lumen into the catheter, and a second orifice that connects this lumen with the vessel space. This allows gas to be introduced through one lumen and into the vessel space, where it can circulate within the vessel space, and then exit the vessel space into the second lumen (FIG. 1).

In FIG. 1, there is depicted an elongate, flexible, relatively non-compliant tube 10 made from a material that is effectively impermeable to carbon dioxide (e.g., polyvinyl chloride plastic). It contains three internal lumens (channels). The left end of tube (as positioned in this illustration) is defined as the distal end, which is placed within an organ or tissue of the patient's body (e.g., by introduction through the nose or mouth or other means). The right end of tube (as positioned in this illustration) is herein defined as the proximal end, and resides within an instrumentation case located at the patient's bedside.

The lower lumen (as it is positioned in this illustration) of the tube is referred to herein as the "pressure" or in-flow lumen 12. Its purpose is to convey gas to the vessel or balloon 14 from the portion of the circuit that is external to the patient, when the system is operating.

The upper lumen (as it is positioned in this illustration) is referred to herein as the "vacuum" or out-flow lumen 16. Its purpose is to convey gas from the balloon 14 to the portion of the circuit external to the patient, when the system is operating.

The middle lumen (as it is positioned in this illustration) is referred to herein as an auxiliary or safety pressure relief lumen 18. Depending on the organ or tissue in which the catheter is placed, the safety pressure relief lumen 18 may be used for removing fluid from the organ or tissue, or for delivering drugs or nutrients to the organ or tissue. For example, if the catheter is placed by way of the nose into the stomach, then the safety pressure relief lumen may be used for any conventional purpose that a standard nasogastric tube could be used (e.g., to deliver nutrients or drugs to the stomach, or for aspirating stomach contents).

The vessel 14, which may be configured as an inflatable balloon, is made from a silicone elastomer or other membranous material that is permeable to carbon dioxide. Open (i.e., white) arrows within the vessel space indicate flow of gas from the pressure lumen 12 via the in-flow orifice 20 to the vacuum lumen 16 via the out-flow orifice 22.

The syringe 38 and stopcock 34 are necessary only if an inflatable vessel is to be used. An advantage of employing an inflatable vessel is that increased measurement efficiency will prevail (in the inflated state) due to the increase in surface area and decrease in thickness of the carbon dioxide permeable membrane. At the same time, an inflatable vessel minimizes the size or diameter of the distal end of the catheter (in the deflated state), an advantage because catheter insertion may be facilitated by a smaller size or diameter of the vessel and distal catheter.

The orifice 22 connects the vessel space and vacuum lumen of the tonometry catheter. Gas within vessel space is aspirated from the vessel space by way of this orifice. The orifice 20 connects the vessel space and pressure lumen of the tonometry catheter. Gas is pumped from the pressure lumen into the vessel space by way of this orifice. It should be noted that the catheter could work equally well if the direction of gas flow were opposite to that depicted. Accordingly, the orifice 22 could be upstream of the orifice 20, or the direction of gas flow could be reversed.

The reference numeral 24 designates the distal end orifice of the safety pressure relief lumen, which may alternatively or in addition be provided with one or more side orifices 26. As in conventional medical practice, several side orifices may be provided to obviate occlusion of all safety pressure relief lumen orifices by contact with tissue during aspiration via the external end of the safety pressure relief lumen, if such aspiration capability should be desired.

The proximal (i.e., extracorporeal) end of the safety pressure relief lumen 18 can optionally be connected to a suction pump for aspirating liquid or gas from the organ or tissue in which the catheter has been placed. Alternatively, it can be connected to a syringe, infusion pump, or other delivery system for introducing drugs or liquid nutrients into the tissue or organ.

An optional pressure relief valve 30 serves as a safety device in the event of a malfunction that results in a build up of pressure within the tissue or organ while the external end 28 of the safety pressure relief lumen is occluded.

An optional pressure transducer 32 may sense and quantify the pressure within the safety pressure relief lumen and serve as a means of indicating an abnormal increase in pressure within the tissue or organ that may be due to malfunction of the device.

At region 34, the vacuum lumen is a separate tube (i.e., separated from the three-lumen portion of the tonometry catheter).

A stopcock 36 is opened only for balloon inflation; i.e., during system initialization. This stopcock is closed once the balloon is inflated, thus maintaining a closed recirculating gas circuit during system operation. This stopcock is optional if a non-inflatable vessel is employed.

A syringe 38 is provided for introducing extra gas (air) into the circuit during system initialization in order to inflate the balloon. This syringe is optional if a non-inflatable vessel is employed.

For circulating gas in one direction through the closed circuit system, a pump 40 is provided as a means for propelling gas. The pump can be a peristaltic pump, roller pump, diaphragm pump, impeller pump, or other type of pump. The direction of gas flow is illustrated by the open (i.e., white) arrow shown immediately to the right and below the pump. However, the invention could function equally well if the direction of flow were reversed.

Optionally, a pressure relief valve 42 may be intercalated anywhere downstream of the pump to act as a safety device in event of a system malfunction that results in gas exiting the closed circuit system and entering the patient's body. For example, this situation could prevail if the following events occurred:

(1) some portion of the vacuum lumen 16 became occluded upstream, and (2) the vacuum lumen 16 ruptured or otherwise became open to the atmosphere between the pump 40 and the point of the aforementioned occlusion, and (3) the safety pressure relief lumen(s) 18, or the proximal 28 or distal 24 and 26 openings of the safety pressure relief lumen(s) all became occluded, or if these openings or lumen(s) were of insufficient caliber to vent gas pumped into the organ or tissue surrounding the catheter, or if these openings were not in proximity or communication with the gas pumped into the organ or tissue, or (4) the pressure relief valve 30 malfunctions or becomes occluded. Each condition may be effectively ameliorated by the valve 42.

For sensing and quantifying the pressure within the lumen of the circuit, a pressure transducer 44 may be provided anywhere in the circuit downstream of the pump. This serves as a means of indicating an abnormal increase in pressure within the circuit that may be due to over-pressurization or device malfunction. It also serves to indicate when the balloon is inflated, and when the balloon is deflated, if an inflatable vessel is used. During operation, it also serves to indicate when there is low pressure within the system, which may be indicative of inadequate pressurization or loss of integrity of the circuit. The output of this sensor may be used to control operation of the pump; e.g., turning it off if the pressure exceeds a certain value.

A means for quantifying the partial pressure, or a sensor (e.g., employing infrared spectroscopy) may be provided at any point in the internal or external portion of the recirculation circuit to measure the percentage (or partial pressure) of carbon dioxide gas within the tubing of the recirculating gas circuit. The sensor 46 may sense the level, percentage, proportion, or partial pressure of carbon dioxide gas within the circuit. Such sensor may include any type of non-destructive carbon dioxide sensor, such as an infrared spectroscopic carbon dioxide sensor, a spectrophotometric sensor, an optical dye sensor, a polarographic electrode sensor, a fluorescent optode carbon dioxide sensor, or other type of $CO_2$ gas sensor which may be situated within the closed space of the tonometry circuit or outside thereof.

Alternatively, to provide a means for measuring and quantifying the level, percentage, proportion, or partial pressure of $CO_2$ gas within the circuit, a capnometer, capnograph, or other similar device may be provided. Such a device is generally electrically or optically connected to the $CO_2$ sensor, or is an integral part of the $CO_2$ sensor. Preferably, the $CO_2$ measurement device is a mainstream capnograph. Alternatively, a sidestream capnograph may be used.

Preferably, the sensor 46 communicates with a circuit that provides a means for controlling the capnometer display or capnograph, and triggers a signalling device which emits an audible or generates a visual alarm when certain values are exceeded or fall below pre-selected values.

At region 48, the pressure lumen is a separate tube (i.e., separated from the three-lumen portion of the tonometry catheter).

An electronic circuit is represented by the box 50. It includes a power supply, spectroscopy electronics, an audible alarm device, a microprocessor for performing calculations, controlling the pump, and driving a display screen if one is used. The circuit is powered via an electrical power cable 52 and may also be battery operated. Another electrical cable 54 provides power to pump. Cables 56 and 58, respectively, are cables that connect the circuit to the pressure transducer 44 and carbon dioxide sensor 46 to the electronic circuit. The cable 60 connects the safety pressure relief or auxiliary lumen pressure transducer to the electronic circuit.

A control and display panel is represented by the reference numeral 62. An electrical cable 64 connects the control and display panel to the electronic circuitry. A push-button or pressure-sensitive keyboard 66 allows entry of blood bicarbonate concentration and alarm limits. The control panel 62 provides a means for entering the value of blood, serum or plasma bicarbonate concentration, critical value alarm limits, and other information by a keyboard, key pad, push buttons, electrical or electronic switches, or other input devices. Additionally, the display panel 62 may provide a means for displaying the results of values derived from any one or combination of the following in digital, analog, graphical, or other form using lights, light emitting diodes, a cathode ray tube, liquid crystal display, a printer, or other means of display: the blood, serum or plasma bicarbonate concentration; and the measured value of the level, percentage, proportion, and partial pressure of $CO_2$ gas within the closed recirculation circuit. Ideally, the control and display panel 62 also includes a means for selecting the configuration of the displayed results, including a choice of digital, analog, graphical, textural, or other form indicating the entered, measured, and/or derived values.

A power switch 68 is provided on the unit 62. One of several push-button type function switches 70 may be included to enable an operator to select display options, prompt appearance of instructions on the display screen, etc.

The electronic display (e.g., liquid crystal matrix or LCD) 72 screen or other visual output device displays the results of tissue $pCO_2$ measurements and/or tissue pH. This output device may also provide a graphical display of tissue $pCO_2$ measurements and/or tissue pH with respect to time, provide textual information regarding the operation of the invention, indicate alarm conditions, and prompt the user for input of information by way of component 66 or component 70.

Thus, a continuous CRGT monitoring system has been devised using an improved balloon-tipped, nasogastric tube, coupled to or integral with an extracorporeal, gas-tight circuit incorporating a pump and a carbon dioxide ($CO_2$) analyzer. All of this is configured as a closed recirculation system.

In more detail, the gastric tonometry catheter of the present invention comprises an elongate, flexible, relatively non-compliant, multilumen tube having a proximal, extracorporeal end and a distal, intracorporeal end. The tube itself, and the septa that separate its lumens, are constructed from a material that is effectively impermeable to carbon dioxide gas (e.g., polyvinyl chloride plastic). The distal end has a tonometry vessel, which may be distensible, situated adjacent thereto. The vessel is constructed from a membranous material (e.g., silicone elastomer) that is effectively permeable to carbon dioxide gas, but effectively impermeable to liquid. The vessel defines a space contained within the wall or membrane from which the vessel is made, and surrounding a portion of the tube of the tonometry catheter, which may be filled with gas.

The vessel space in-flow orifice lies in communication with the vessel space, through which gas may enter the vessel. A vessel in-flow lumen, also referred to as the pressure lumen, is provided within the tonometry catheter. This lumen has a distal end and a proximal end. The distal end of the pressure lumen is disposed in communication with the vessel space in-flow orifice.

The vessel space out-flow orifice is provided in the tonometry catheter and lies in communication with the vessel space, through which the gas may leave the vessel. The vessel out-flow lumen, also referred to as the vacuum lumen, is provided within the tonometry catheter. This lumen has a distal end and a proximal end. The distal end is disposed in communication with the vessel space out-flow orifice.

In addition to the pressure lumen and the vacuum lumen, a third lumen may optionally be incorporated within the tonometry catheter. This third lumen is herein referred to as the safety pressure relief or auxiliary lumen. The safety pressure relief lumen has a distal end and proximal end. The distal end opens into one or several orifices at the distal end of the tonometry catheter. One of these distal orifices may be located at the distal tip of the tonometry catheter. One or more additional distal orifices may be located along the side of the tonometry catheter near its distal tip. None of the orifices of the safety pressure relief lumen communicate with the balloon space. None of the orifices of the safety pressure relief lumen communicate with the pressure lumen, and none of the orifices of the safety pressure relief lumen communicate with the vacuum lumen.

In use, the proximal end of the safety pressure relief lumen may be sealed with a clamping device or otherwise be occluded. Alternatively, it may be utilized for a variety of purposes that are conventionally used in the diagnosis and treatment of acutely ill hospitalized patients. When the organ in which the catheter is placed is the stomach, these may include connection of the proximal end of the safety pressure relief lumen to a suction pump for aspirating stomach contents as a diagnostic or therapeutic maneuver; or connection to a syringe, infusion pump, or other delivery system for introducing drugs or liquid nutrients into the stomach. A pressure relief valve may optionally be intercalated within or attached to the extracorporeal portion of the safety pressure relief lumen, the purpose and function of which is explained below. A sensor, transducer or other means of monitoring the pressure within the auxiliary lumen may optionally be intercalated within or attached to the safety pressure relief lumen, the purpose and function of which is explained below.

The proximal end of the vacuum lumen and the proximal end of the pressure lumen are connected together to form a closed circuit. Within this portion of the circuit may lie a stopcock and attached syringe (or other means of introducing additional gas or otherwise pressurizing the circuit), which are necessary it a distensible tonometry vessel is used. Also within this portion of the circuit lies a pump, an optional pressure relief valve, an optional device to monitor the pressure within the lumen of the circuit, and a sensor capable of detecting and quantifying the concentration, percentage or partial pressure of carbon dioxide within the circuit.

The purpose of the syringe or alternative pressurizing device is to introduce additional gas into the circuit so as to increase the pressure within the circuit and effect distension or inflation of the tonometry vessel. This is necessary if a distensible tonometry vessel is used but is otherwise optional. Such inflation is normally not performed until the distal end of the catheter is placed within the patient's body at a suitable location. The stopcock is provided to trap the introduced gas within the circuit during operation after the syringe is used to effect vessel inflation. The stopcock and syringe are also used to remove trapped gas from the circuit, thereby deflating the distended vessel. This is performed by opening the stopcock and aspirating the added gas from the circuit.

The carbon dioxide gas sensor is any type of device that detects and quantifies, directly or indirectly, the concentration, percentage or partial pressure of carbon dioxide gas within the circuit. This may employ infrared spectroscopy, indicator dye-based spectrophotometry, polarographic electrodes, fluorescent optodes, or other nondestructive methods of carbon dioxide gas analysis that can be performed on gas mixtures within a closed system. The final output of the sensor consists of an electrical signal that is proportional (with respect to voltage, current, frequency, phase or other electrical property) to the concentration, percentage or partial pressure of carbon dioxide within the circuit.

The pump is employed to cause the circulation of gas within the closed circuit of the system. The pump may consist of a peristaltic pump, roller pump, diaphragm pump, impeller pump, or other type of pump suitable for propelling gas through hollow tubes at any rate of flow, including zero flow. At zero flow, movement of gas within the circuit is effected by diffusion rather than convection.

In summary, the vessel, the pressure lumen, and the vacuum lumen, with the intercalated pump and the carbon dioxide sensor, define a closed path through which the enclosed gas may continuously diffuse or recirculate. This closed circuit system provides a means of continuously monitoring the level of carbon dioxide gas within an organ or tissue of the body. The level of carbon dioxide gas within most tissues or organs (expressed as the partial pressure of carbon dioxide gas, or $pCO_2$) is, in most undisturbed circumstances known to be equivalent to the $pCO_2$ within the cells of the tissue or organ. Thus, the CRGT allows continuous monitoring of tissue $pCO_2$.

From tissue $pCO_2$, tissue pH (also known as intracellular pH or pHi or the negative logarithm of intracellular hydrogen ion concentration) may be calculated from the equation of Henderson and Hasselbalch. Henderson L. J., "The Theory Of Neutrality Regulation In The Animal Organism," 21 AMERICAN JOURNAL OF PHYSIOLOGY 427 (1908); Hasselbalch K. A., "Die Berechnung der Wasserstoffzahl des Blutes aus der freien und gebundenen Kohlensäure desselben, und dieSauerstoffbindung des Blutes als Funktion der Wasserstoffzahl," 78 Biochem Z. 112 (1916); and Kruse J. A., "Relationship Between The Apparent Dissociation Constant Of Blood Carbonic Acid And Severity Of Illness, " 114 J. Lab. Clin. Med. 568–574 (1989) as follows:

$$pHi = pK' + \log_{10} \frac{[HCO_3^-]}{s \times pCO_2}$$

where "pK'" is the apparent first dissociation constant of carbonic acid (a constant equal to approximately 6.1), "s" is the solubility coefficient (also known as Bunsen's coefficient) of carbon dioxide gas in physiological solution (a constant approximately equal to 0.03 mmol/L per torr at 37° C.), and "$[HCO_3^-]$" is the molar concentration of bicarbonate inside the cells of the tissue or organ. The latter is held to be equal to or closely approximated by the molar concentration of bicarbonate in blood, plasma or serum.

Thus, if arterial bicarbonate concentration is known, tissue pH (pHi) can be determined mathematically using the Henderson-Hasselbalch equation and the value of tissue $pCO_2$ determined by CRGT.

The CRGT system described herein can be provided with electronic circuitry to display the determined value of tissue $pCO_2$, either as a digital or analog readout, or graphical on a cartesian coordinate system using $pCO_2$ as the ordinate and time as the abscissa. This CRGT system can also be provided with electronic circuitry to automatically perform the calculation of tissue pH and display its value in similar fashion.

A potential malfunction is considered in which any of the following events occur: (1) the balloon ruptures, allowing gas from the recirculation circuit to enter the tissue or organ; (2) the vacuum lumen becomes occluded at some point between its distal end and the point of connection with the pump; (3) the pump or its inflow tube connection becomes open to the atmosphere at some point between the aforementioned occlusion and the outflow portion of the pump; (4) the proximal end of the safety pressure relief lumen is occluded or otherwise not open to the atmosphere; (5) the pump is allowed to operate.

If all of these circumstances were to occur at one time, gas could be pumped into the tissue or organ under pressure and result in gaseous distention of the tissue or organ, a potentially undesirable physiological condition. The optional pressure relief valve located on the extracorporeal portion of the safety pressure relief lumen allows excessive tissue or organ pressure to be vented from the tissue or organ to the atmosphere. The pressure at which this relief valve opens is such that the valve is unlikely to open at pressures that can occur under normal physiologic conditions, but such that it will open if a higher degree of tissue or organ pressure should occur.

A similar, also optional, pressure relief valve may be intercalated within the extracorporeal portion of the recirculating gas circuit. This optional pressure relief valve serves the same purpose as the one on the safety pressure relief lumen. However, this second pressure relief valve opens at a different pressure, namely a pressure that exceeds the normal working pressure of the recirculating gas circuit. This pressure threshold may be higher than the threshold used by the relief valve located on the safety pressure relief lumen.

Sensors, transducers, or other devices (e.g., electronic strain gauge transducers, pressure activated electrical switches, pressure gauges, or other pressure activated mechanical, electrical, or electromechanical device) that convert pressure into a signal indicating the relative or absolute value of pressure may optionally be intercalated within or otherwise attached to the safety pressure relief lumen and/or the lumen of the circuit. The sensor in communication with the safety pressure relief lumen will serve to indicate a condition of abnormally high pressure within the safety pressure relief lumen that may indicate a device malfunction. The sensor provides a signal before or when the pressure relief valve opens, thus alerting the operator that a malfunction may have occurred. The similar, also optional, pressure sensor of the gas recirculation circuit may serve to indicate when the pressure within the circuit is equal to atmospheric pressure (indicating that the circuit is not pressurized), when the circuit is inadequately pressurized, when the circuit is adequately pressurized, when the vessel is inflated (if a distensible vessel is employed), when the vessel is deflated (if a distensible vessel is employed), and when the circuit is over-pressurized (as could occur in the case of device malfunction).

Performance of the capnometric recirculating gas tonometry (CRGT) system was validated in vivo in seven anesthetized and mechanically ventilated dogs weighing 15 to 22 kilograms. For each experiment, the distal end of the CRGT catheter was placed in the animal's stomach (by way of the mouth) and connected to the extracorporeal instrument portion of the CRGT apparatus, as previously described. A second prior art catheter was also placed in the animal's stomach and saline solution was instilled into its chamber. Thus, the CRGT system was used to continuously monitor gastric intramucosal $pCO_2$ and pH. The purpose of the conventional intermittent tonometry catheter was to obtain independent measurement of gastric intramucosal $pCO_2$ and pH using this prior art for comparison. Within the time frame of these experiments, the conventional tonometry catheters only allow a single measurement to be made, and therefore do not allow continuous monitoring.

Using CRGT, $pCO_2$ was recorded at 5-minute intervals for 30 minutes. At the end of the 30-minute partial equilibration period, the saline solution was aspirated from the conventional tonometry catheter and analyzed for $pCO_2$ using a laboratory blood gas analyzer (model ABL-2; Radiometer, Inc.; Westlake, Ohio). Using the equation:

$$[HCO_3^-] = S \times pCO_2 \times 10^{(pH-pK')},$$

the same instrument was used to determine bicarbonate concentration from an arterial blood specimen of each animal (Kruse, J. A., et al., "Relationship Between The Apparent Dissociation Constant Of Blood Carbonic Acid And Severity Of Illness," 114 JNL OF LAB. & CLIN. MED. 568–574 (1989).

The $pCO_2$ value obtained at 30 minutes by CRGT was compared to the $pCO_2$ value obtained by laboratory analysis of the saline from the conventional catheter. Gastric intramucosal pH was calculated from the $pCO_2$ values obtained by CRGT and by conventional intermittent tonometry (extrapolated to steady state levels), the arterial blood bicarbonate concentration, the pK' of carbonic acid in blood, the solubility coefficient of carbon dioxide gas in plasma, and the Henderson-Hasselbalch equation.

pCO$_2$ determined by CRGT rose from zero to a near plateau by the end of the 30-minute period. Using repeated measures analysis of variance, Fisher's PLSD multiple comparison statistic, and a two-tailed α probability level of 0.05, the 30-minute pCO$_2$ values obtained by CRGT were not statistically significantly different from the values obtained at 25 minutes, statistically corroborating the plateau. Using Student's paired t test and a two-tailed α probability level of 0.05, the pCO$_2$ values obtained by CRGT at 30 minutes were not statistically significantly different from the pCO$_2$ values obtained at 30 minutes by conventional intermittent tonometry. This indicates agreement with measurements obtained using the prior art.

Similarly, the pH values derived by CRGT at 30 minutes were in close agreement (no statistically significant difference by paired t test) from the pH values obtained at 30 minutes by conventional intermittent tonometry.

Related experiments subsequently performed under hypoxic conditions have shown similar agreement between the two methods, and have also shown that CRGT can identify changes in gastric intramucosal pCO$_2$ and pH within 5 minutes of experimentally induced tissue hypoxia.

Having above indicated a preferred embodiment of the present invention, it will occur to those skilled in the art that modifications and alternatives can be practiced within the spirit of the invention. It is accordingly intended to define the scope of the invention only as indicated in the following claims.

We claim:

1. A tonometry catheter apparatus comprising:
   an elongate flexible tube having a proximal extracorporeal end and a distal intracorporeal end;
   the distal end of the tube having
      a distensible, inflatable, gas-permeable tonometry vessel, the vessel and the distal end defining therebetween a space which is filled with a gas,
      an in-flow orifice in communication with the space, through which gas may enter the vessel,
      an in-flow lumen with a distal end and a proximal end, the distal end being in communication with the in-flow orifice,
      an out-flow orifice in communication with the space, through which the gas may exit the vessel, and
      an out-flow lumen with a distal end and a proximal end, the distal end being in communication with the out-flow orifice,
   the proximal end of the tube having
      means for propelling gas into the vessel, the propelling means being selected from a group consisting of a peristaltic pump, a roller pump, an impeller pump, a blower, a propeller, a fan, a circulator, and their equivalents, and
      means for continuously quantifying the level of carbon dioxide (CO$_2$) gas exiting the vessel, and
      a hollow connecting member linking the propelling and quantifying means to define with the vessel, the in-flow lumen and the out-flow lumen a closed path through which the gas may continuously recirculate under a relatively constant pressure, thereby resulting in a substantially error-free, stable reading.

2. The tonometry catheter apparatus of claim 1, wherein the in-flow orifice is spaced apart from and upstream of the out-flow orifice, thus forcing gas flow through the length of the vessel, thereby enhancing gas mixing and gas diffusion through the vessel wall.

3. The tonometry catheter apparatus of claim 1, wherein the out-flow orifice is spaced apart from and upstream of the in-flow orifice, thus forcing gas flow through the length of the vessel, thereby enhancing gas mixing and gas diffusion through the vessel wall.

4. The tonometry catheter apparatus of claim 1, wherein the means for quantifying the level of CO$_2$ gas is selected from the group consisting of a CO$_2$ sensor, capnometer, or capnograph.

5. The tonometry catheter apparatus of claim 4, further comprising:
   a capnometry means connected to the CO$_2$ sensor, the capnometry means providing an image of pCO$_2$.

6. The tonometry catheter apparatus of claim 5, wherein the means for quantifying provides real time trending information of the gas level in a tissue or organ of interest.

7. The tonometry catheter apparatus of claim 1, further including means for displaying one or more variables indicative of physiological condition of the patient.

8. The tonometry catheter of claim 1, further including one or more safety pressure relief lumens.

9. A tonometry catheter apparatus comprising:
   an elongate flexible tube having a proximal extracorporeal end and a distal intracorporeal end;
   the distal end of the tube having
      a distensible, inflatable, gas-permeable tonometry vessel, the vessel and the distal end defining therebetween a space which is filled with a gas,
      an in-flow orifice in communication with the space, through which gas may enter the vessel,
      an in-flow lumen with a distal end and a proximal end, the distal end being in communication with the in-flow orifice,
      an out-flow orifice in communication with the space, through which the gas may exit the vessel, and
      an out-flow lumen with a distal end and a proximal end, the distal end being in communication with the out-flow orifice,
   the proximal end of the tube having
      means for propelling gas into the vessel,
      means for continuously quantifying the level of carbon dioxide (CO$_2$) gas exiting the vessel,
      a hollow connecting member linking the propelling and quantifying means to define with the vessel, the in-flow lumen and the out-flow lumen a closed path through which the gas may continuously recirculate under a relatively constant pressure, thereby resulting in a substantially error-free, stable reading,
      one or more safety pressure relief lumens, and
      one or more pressure relief valves in communication with in-flow, the out-flow, and the one or more safety pressure relief lumens to regulate pressure within the closed path in the event of malfunction that could otherwise lead to an undesirable and hazardous progressive accumulation of gas within a body cavity of a human subject in which the vessel is inserted.

10. A tonometry catheter apparatus comprising:
    an elongate flexible tube having a proximal extracorporeal end and a distal intracorporeal end;
    the distal end of the tube having
       a distensible, inflatable, gas-permeable tonometry vessel, the vessel and the distal end defining therebetween a space which is filled with a gas,
       an in-flow orifice in communication with the space, through which gas may enter the vessel,
       an in-flow lumen with a distal end and a proximal end, the distal end being in communication with the in-flow orifice, an out-flow orifice in communication with the space, through which the gas may exit the vessel, and an out-flow lumen with a distal end and a proximal end, the distal end being in communication with the out-flow orifice, the proximal end of the tube having means for propelling gas into the vessel, means for continuously quantifying the level of carbon dioxide ($CO_2$) gas exiting the vessel, and a hollow connecting member linking the propelling and quantifying means to define with the vessel, the in-flow lumen and the out-flow lumen a closed path through which the gas may continuously recirculate under a relatively constant pressure, thereby resulting in a substantially error-free, stable reading, one or more safety pressure relief lumens, and a pressure sensing means in communication with the one or more safety pressure relief lumens for quantifying pressure in the closed path and detecting undesirable or hazardous increases in pressure within a body cavity of a human subject in whom the vessel has been inserted.

11. The tonometry catheter of claim 10, wherein the pressure sensing means comprises a pressure transducer.

12. The tonometry catheter of claim 9, including a pressure sensing means in communication with the hollow connecting member.

13. The tonometry catheter of claim 10, including a pressure sensing means in communication with the hollow connecting member.

14. The tonometry catheter of claim 11, including a pressure sensing means in communication with the hollow connecting member.

15. The tonometry catheter of claim 1, further comprising:

one or more safety pressure relief lumens, each having a distal end and a proximal end, each distal end opening into a plurality of orifices, which may be proximate to the distal tip thereof along the tonometry catheter near its distal tip, none of the orifices communicating with the vessel space, or with the pressure lumen, or with the vacuum lumen.

16. The tonometry catheter of claim 1, wherein the gas contained within the closed path comprises ambient air prior to placement of the apparatus within the body of a patient, and thereafter the gas after equilibration comprises a gas mixture having a composition approximating that of body tissues adjacent the vessel.

17. The tonometry catheter of claim 1, wherein the means for propelling gas into the vessel comprises a means for injecting additional gas into the closed path.

18. A method for continuous indirect monitoring of organ or tissue oxygenation, gas exchange, and pH comprising:

providing a catheter having an elongate flexible tube;

introducing the catheter into an organ of interest so that a gas-permeable, inflatable vessel is disposed at a desired sampling site;

positioning the vessel at the sampling site for a length of time sufficient to allow carbon dioxide gas at the sampling site to diffuse across the vessel's wall and into an out-flow lumen provided within the flexible tube;

circulating gas under a relatively constant pressure within a closed circuit defined by the vessel, the in-flow lumen, the out-flow lumen, and a hollow connecting member connecting the in-flow and out-flow lumens;

analyzing gas on a continuous basis within the closed circuit for the level of carbon dioxide gas within the gas mixture contained in the circuit;

determining the intracellular pH of the organ or tissue at or near the sampling site on a continuous basis from the level of carbon dioxide gas and a measure or estimate of body bicarbonate concentration; and determining whether organ or tissue hypercapnia, acidosis, hypoxia, or ischemia are present on the basis of the determination of carbon dioxide gas level within the vessel and on the basis of intracellular pH determination.

19. A method for continuous indirect monitoring of organ or tissue oxygenation gas exchange, or pH comprising:

positioning a tonometry catheter apparatus according to claim 1 into the body of a patient;

providing a continuous recirculation of gas through a closed circuit including the vessel;

introducing gas into the circuit under positive pressure to distend the vessel;

monitoring connections within the circuit to assure integrity thereof as a closed system;

connecting the catheter to a monitoring circuit for monitoring the level, percentage, proportion, or partial pressure of $CO_2$ gas within the circuit;

allowing entry of the bicarbonate ion concentration of the blood, serum, or plasma into the electronic portion of the system;

deriving the value pH or related values from the measured level, percentage, proportion, or partial pressure of $CO_2$ gas within the circuit and the entered value of the concentration of bicarbonate ions in the blood, serum, or plasma;

displaying and/or recording the measured and/or derived values on a continuous basis; and triggering an audible or visual alarm when a malfunction in the system is sensed, or when the measured or derived values are above or below pre-selected critical values.

20. The method of claim 18, further comprising the step of inserting the catheter by a transnasal, transoral, transrectal, surgical, or other route of placement into some portion of the gastrointestinal tract, which includes the esophagus, stomach, duodenum, small intestines, jejunum, ileum, colon or large intestine, or rectum.

* * * * *